United States Patent
Boue et al.

(10) Patent No.: US 9,874,440 B2
(45) Date of Patent: Jan. 23, 2018

(54) METHOD FOR ASSESSING THE DEPTH OF A CRACK

(71) Applicants: CENTRE NATIONAL DE LA RECHERCHE SCIENTIFIQUE, Paris (FR); UNIVERSITE PIERRE ET MARIE CURIE (PARIS 6), Paris (FR)

(72) Inventors: Christine Boue, Noisy le Grand (FR); Gilles Tessier, Paris (FR); Jean-Paul Roger, Cachan (FR); Mihaela Streza, Cluj Napoca (RO)

(73) Assignees: CENTRE NATIONAL DE LA RECHERCHE SCIENTIFIQUE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 342 days.

(21) Appl. No.: 14/429,425

(22) PCT Filed: Sep. 20, 2013

(86) PCT No.: PCT/FR2013/052185
§ 371 (c)(1),
(2) Date: Mar. 19, 2015

(87) PCT Pub. No.: WO2014/044986
PCT Pub. Date: Mar. 27, 2014

(65) Prior Publication Data
US 2015/0241212 A1    Aug. 27, 2015

(30) Foreign Application Priority Data
Sep. 24, 2012 (FR) .................................. 12 58940

(51) Int. Cl.
*G01N 25/72* (2006.01)
*G01B 21/18* (2006.01)
(Continued)

(52) U.S. Cl.
CPC .............. *G01B 21/18* (2013.01); *G01B 11/22* (2013.01); *G01N 25/00* (2013.01); *G01N 25/72* (2013.01)

(58) Field of Classification Search
USPC ............... 250/252.1, 341.6, 559.39; 356/432
See application file for complete search history.

(56) References Cited

U.S. PATENT DOCUMENTS 5,136,172 A * 8/1992 Nakata ............... G01N 21/1702
250/559.39
5,376,793 A    12/1994 Lesniak
(Continued)

OTHER PUBLICATIONS

Schlichting et al: "Crack sizing by laser excited thermography" (Sep. 23, 2011).
(Continued)

*Primary Examiner* — Lam Nguyen
(74) *Attorney, Agent, or Firm* — IPSilon USA, LLP

(57) ABSTRACT

The invention relates to a method for assessing the depth of a crack near the surface of a material, characterized in that said method includes the following steps: heating an area located near the crack using of a heat source (2) that is periodically modulatable into a heat flow at a controllable frequency, a so-called "modulation frequency", varying the frequency so as to vary the heat diffusion length between an initial value, less than the distance between the heated area and the crack, and a final value that is greater than the distance between the heated area and the crack; determining the variation, depending on the heat diffusion length, in a function on the basis of at least one derivative, relative to a space variable, of the amplitude of the sinusoidal component of the temperature, on the surface of the material and at the modulation frequency, at each point of a set of points of the crack so as to cause a first area of variation in the function to appear, wherein said function increases at a first nonzero (Continued)

slope, followed by a second variation area, wherein said function increases at a second slope, different from the first slope; and assessing the depth of the crack on the basis of the value of the heat diffusion length at the intersection of the first variation area and the second variation area, the so-called "intersection length".

11 Claims, 1 Drawing Sheet

(51) Int. Cl.
*G01B 11/22* (2006.01)
*G01N 25/00* (2006.01)

(56) References Cited

U.S. PATENT DOCUMENTS

| | | | | |
|---|---|---|---|---|
| 5,479,259 | A * | 12/1995 | Nakata | G01K 5/52 356/432 |
| 7,060,971 | B2 * | 6/2006 | Zombo | G01N 25/72 250/252.1 |
| 2004/0041096 | A1 * | 3/2004 | Sun | G01N 25/72 250/341.6 |

OTHER PUBLICATIONS

Nakata et al: "Simulation of photoacoustic imaging of microcracks in silicon wafers using a structure-changeable multi layered thermal diffusion model" (Mar. 1, 2007).

Lahiri et al: "Quantification of defects in composites and rubber materials using active thermography" (Jan. 21, 2012).

Search Reported dated 2013.

"Depth estimation of surface cracks on metallic components by means of lock-in thermography" Streza et al. dated 2013.

* cited by examiner

METHOD FOR ASSESSING THE DEPTH OF A CRACK

RELATED APPLICATIONS

This application is a National Phase Application of PCT/FR2013/052185, filed on Sep. 20, 2013, which in turn claims the benefit of priority from French Patent Application No. 58940 filed on Sep. 24, 2012, the entirety of which are incorporated herein by reference.

BACKGROUND

Field of the Invention

The subject of the present invention is a method for assessing the depth of a crack near the surface of a material, in particular of a metallic material. Also the subject of the invention is a method that makes it possible, in addition to assessing the depth of the crack, to locate said crack.

Description of Related Art

The detection of defects on the surface of metallic parts, such as, for example, cracks, and their qualification and the estimation of their dimensions, is done typically using the dye penetration technique.

However, this technique is polluting and is subject to human assessment, which generates problems of repeatability and means that it cannot be automated. It therefore seems important to find an objective and robust technique that makes it possible to detect and provide reliable information on the depth of the cracks, in the context of a non-destructive inspection on an industrial scale.

OBJECTS AND SUMMARY

The present invention makes it possible to achieve these objectives.

Thus, the subject of the invention is a method for assessing the depth of a crack near the surface of a material.

The method according to the invention comprises the following steps:
heating a zone situated in proximity to the crack, using a heat source whose heat flux can be periodically modulated according to an adjustable frequency, called modulation frequency,
varying the frequency, so as to vary the heat diffusion length between an initial value less than the distance between the heated zone and the crack and a final value greater than the distance between the heated zone and the crack,
the value of the heat diffusion length being given By the relationship:

$$\mu = a \cdot (D/f)^{1/2}$$

in which:
$\mu$ designates the heat diffusion length, a designates a real constant, D designates the thermal diffusivity of the material in m²/s, and f designates the modulation frequency of the periodic heat source in Hz,
determining the trend, as a function of the heat diffusion length, of a function based on at least one derivative, relative to a space variable, of the amplitude of the sinusoidal component of the temperature on the surface of the material and at the modulation frequency, at each of the points of a set of points of the crack, so as to reveal a first trend zone of the function in which said function increases according to a first non-zero slope, followed by a second trend zone in which said function increases according to a second, slope different from the first slope, and
assessing the depth of the crack, as a function of the value of the heat diffusion length at the intersection of the first trend zone and of the second trend zone, called intersection length.

In the case of a sinusoidal modulation of the heat flux, the value of the heat diffusion length can be given by the relationship:

$$\mu = \sqrt{\frac{D}{\Box \pi f}}$$

The set of points can comprise one or preferably several points so as to more accurately determine the trend of the function.

The trend of the function can be obtained by producing an average or applying a mathematical treatment to the trends of the function obtained for the set of points.

The distance between the heated zone and the crack can be estimated by any value representative of this distance, for example by the shortest distance between the heated zone and the crack, or even by the distance between the barycenter of the heated zone and the crack.

Said function can be the Laplacian applied to the amplitude of the sinusoidal component of the temperature at the modulation frequency.

The intersection length can, for example, be obtained by applying a criterion dependent on the place of slope change. It is possible, for example, to determine the point of intersection of the trend curve of the function and of a selected curve secant to the function in its slope change zone. It is also possible to adjust the trend curve of the function by a mathematical function of which one of the parameters makes it possible to obtain the intersection length. At least one of the parameters of said mathematical function can, for example, be determined from, the trend as a function of the heat diffusion length, of a function (which can be based on at least one derivative, relative to a space variable) of the phase of the sinusoidal component of the temperature on the surface of the material and at the modulation frequency.

The depth of the crack can be estimated using the following relationship:

$$h^* = (\mu_2^2 - d^2)^{1/2}$$

in which $\mu_2$ designates the intersection length and d designates the distance between a given point of the crack and the closest point of the heat source.

The heat source can be created by the absorption on the surface of the material of a light flux from a light source, or by a component using the Peltier effect or the Joule effect.

The light source can be a laser source or an arc lamp, or a filament lamp.

The heating zone located in proximity to the crack can be located at a distance from the edge of the crack of between 0.5 and 2 mm.

The frequency can vary between 0.1 Hz and 20 Hz.

The method can use a thermal camera.

The method can further comprise a step of detection of the crack.

The detection of the crack can be obtained by implementing, at different points of a zone surrounding the crack, a temporal Fourier transform of the temperature at each point, followed by a calculation of the Laplacian (or of another function using at least one spatial derivative) of the amplitude of the sinusoidal component of the temperature at the modulation frequency.

BRIEF DESCRIPTION OF THE DRAWINGS

Other features and advantages of the present invention will become more clearly apparent on reading the following description given as an illustrative and nonlimiting example and done so with reference to the following figures in which.

DETAILED DESCRIPTION

Figure 1:
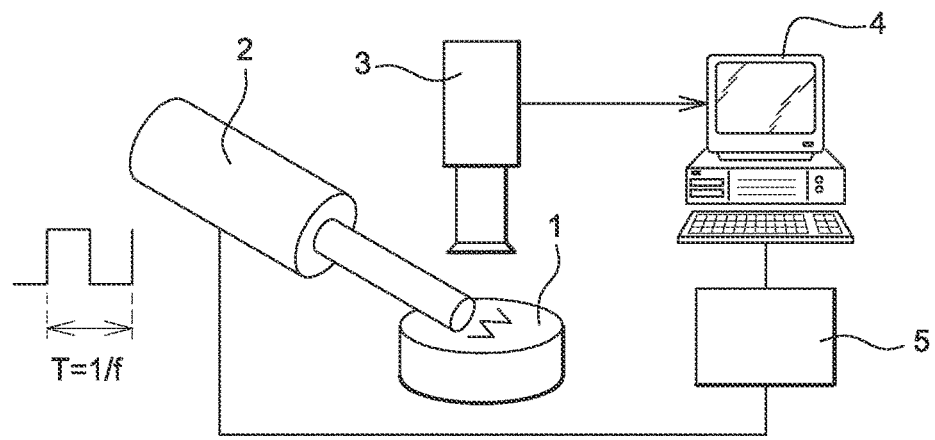
FIG. 1 schematically illustrates a device that makes it possible to implement the method according to the invention.

As illustrated in FIG. 1, a metal sample 1 is heated periodically using a heat source 2. The thermal images are input using an infrared camera 3 coupled to a computer 4. A synchronous detection module 5 computes, in real time, the phase and the amplitude of the physical phenomenon at the modulation frequency. The module 5 also makes it possible to obtain images in amplitude and in phase at the harmonic frequencies of the modulation frequency.

To locate the cracks of the sample 1, a digital processing operation is applied to the image of the amplitude. It is possible for example:

to derive the image of the amplitude in x or in y (in the plane xy of the surface of the sample) if a direction is to be prioritized, to proceed with a computation of the Laplacian, if direction is not to be prioritized, to proceed to process the resulting image.

The sample 1 is heated by the heat source 2 with an excitation modulated at modulation frequencies from 0.1 to 20 Hz and generally focused on a zone of a few mm in diameter. The heat source 2 is placed in such a way as to excite the face of the sample 1 to be inspected.

The infrared signal is detected by the infrared camera 3 in synchronous detection mode. The measurement time depends on the number of cycles averaged. It is generally a few seconds.

The next part of the description is devoted to assessing the depth of a crack near the surface of the sample 1.

When a material is heated locally on the surface, the heat diffuses on the surface and depthwise. If the heat stimulus is periodic, the sinusoidal component of the heat flux at the modulation frequency extends over a heat diffusion length which depends on the thermal diffusivity of the material and on the modulation frequency. When there is a crack, the heat flux is locally disturbed. A temperature rise then occurs upstream of the crack.

The next part of the description relates to modulations, therefore ideal and simple configurations, but which largely apply to more realistic and complex cases.

The case of an emerging crack, normal to the surface, of width $l_{fiss}$, of length $L_{fiss}$ and of depth h, is considered, The cracked sample is heated on the surface by a heat flux modulated at the frequency $f_i$. The distance between the heat source and the crack is given by d. At the modulation frequency $f_i$, the sinusoidal component of the heat flux extends on the surface and in the thickness of the sample over a heat diffusion length $\mu_i$ such that:

$$\mu_i = \sqrt{\frac{D}{\pi f_i}}$$

For a fairly low modulation frequency, the sinusoidal component of the heat flux extends over a greater length than if the modulation frequency is high.

Figure 2:
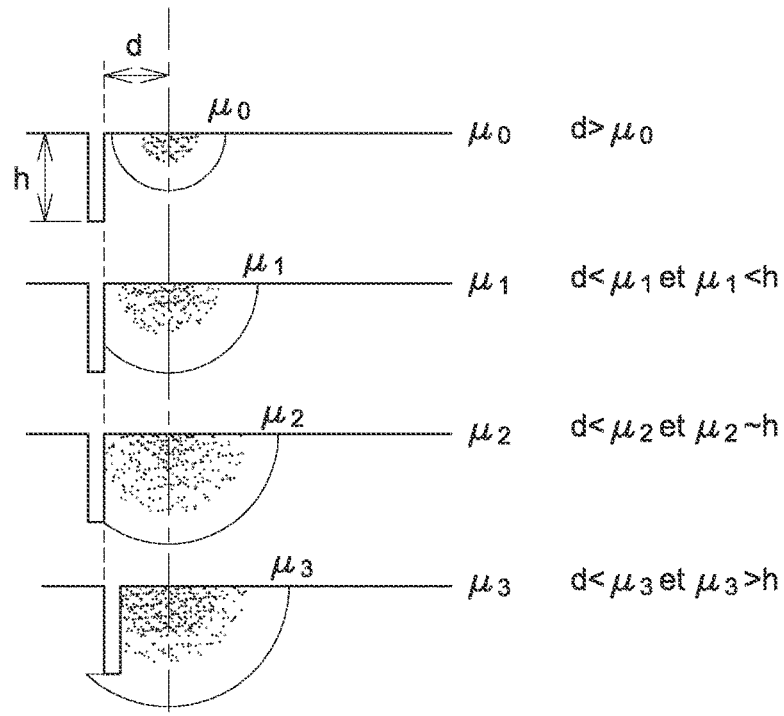
FIGS. 2 and 3 are different diagrams useful to the understanding of the method.

The following are thus observed, as illustrated in FIG. 2:

for the diffusion lengths $\mu_0$ that are small compared to the distance d, the sinusoidal component of the heat flux, represented by a half-disk, and for more clarity for values greater than a predetermined threshold, does not reach the crack, for the diffusion lengths $\mu_1$ of the order of magnitude of d, the sinusoidal component of the heat flux reaches the crack on the surface and partially in volume, for a diffusion length substantially equal to the depth h of the crack, the sinusoidal component of the heat flux reaches the crack on the surface and entirely in volume, and for the diffusion lengths $\mu_3$ greater than d and than the depth h of the crack, the sinusoidal component of the heat flux extends in volume beyond the crack of depth h.

The presence of a crack disturbs the heat flux. The Laplacian of the amplitude of the temperature T on the surface $L=\nabla^2(T)$ is chosen as parameter revealing the crack. Unlike the gradient for example, it includes any direction on the surface if direction is not to be prioritized.

Figure 3:
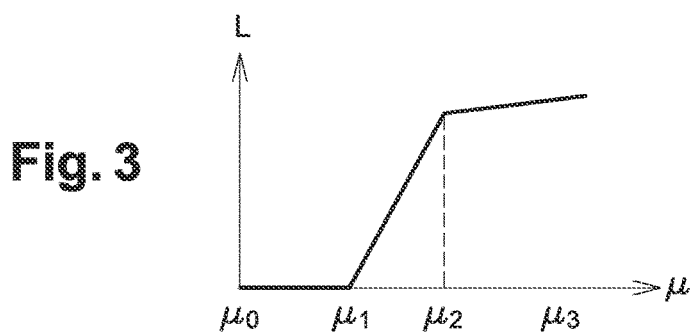

Schematically, for a point of the crack, the trend of L as a function of $\mu$ can be plotted, as illustrated in FIG. 3:

for the diffusion lengths that are small compared to the distance d, L tends toward zero: the crack is not reached, for the diffusion lengths that make it possible to reach the crack on the surface and partially in volume, L increases, and for the diffusion lengths greater than $(d^2+h^2)^{1/2}$, L increases more slowly: a part of the heat flux circumvents the crack.

The change of slope of the curve of the trend of the Laplacian of the amplitude of the sinusoidal component of the temperature at the modulation frequency as a function of $\mu$ (here for $\mu$ which is situated, in a region close to $\mu_2$) constitutes an indicator of the value h of the depth of the crack. If d designates the distance between the point considered on the crack and the closest point of the heat source, then the estimated value h* of the depth of the crack is given by the relationship:

$$h^* = \sqrt{\mu_2^2 - d^2}$$

The idea, which is to assess the depth of a crack from the curve of the trend of the Laplacian of the amplitude of the sinusoidal component of the temperature at the modulation frequency as a function of the frequency, is easy to transpose from the experimental point of view by using measurements obtained at different heating frequencies.

The invention claimed is:

1. A method for assessing the depth of a crack near the surface of a material, said method comprising the steps of:

heating a zone situated in proximity to the crack, using a heat source whose heat flux can be periodically modulated according to an adjustable frequency, called modulation frequency, varying the frequency, so as to vary the heat diffusion length between an initial value less than the distance between the heated zone and the crack and a final value greater than the distance between the heated zone and the crack, the value of the heat diffusion length being given by the relationship:

$$\mu = a \cdot (D/f)^{1/2}$$

in which:

μ designates the heat diffusion length, a designates a real constant, D designates the thermal diffusivity of the material in m²/s, and f designates the frequency of the periodic heat source in Hz, determining the trend, as a function of the heat diffusion length, of a function based on at least one derivative, relative to a space variable, of the amplitude of the sinusoidal component of the temperature on the surface of the material and at the modulation frequency, at each of the points of a set of points of the crack, so as to reveal a first trend zone of the function in which said function increases according to a first non-zero slope, followed by a second trend zone in which said function increases according to a second slope different from the first slope, and assessing the depth of the crack as a function of the value of the heat diffusion length at the intersection of the first trend zone and of the second trend zone, called intersection length.

2. The method as claimed in claim 1, wherein said function is the Laplacian applied to the amplitude of the sinusoidal component of the temperature at the modulation frequency.

3. The method as claimed in claim 1, wherein the trend curve of the function is adjusted by a mathematical function, of which one of the parameters makes it possible to obtain the intersection length.

4. The method as claimed in claim 3, wherein at least one of the parameters of said mathematical function is determined from the trend, as a function of the heat diffusion length, of a function of the phase of the sinusoidal component of the temperature on the surface of the material and at the modulation frequency.

5. The method as claimed in claim 1, wherein the depth of the crack is estimated using the following relationship:

$$h^* = (\mu_2^2 - d^2)^{1/2}$$

in which $\mu_2$ designates the intersection length and d designates the distance between a given point of the crack and the closest point of the heat source.

6. The method as claimed in claim 1, wherein the heat source is created by the absorption on the surface of the material of a light flux from a light source, or by a component using the Peltier effect or the Joule effect.

7. The method as claimed in claim 1, wherein the heating zone located in proximity to the crack is located at a distance from the edge of the crack of between 0.5 and 2 mm.

8. The method as claimed in claim 1, wherein the frequency varies between 0.1 Hz and 20 Hz.

9. The method as claimed in claim 1, wherein said method further employs a thermal camera.

10. The method as claimed in claim 1, wherein said method further comprises a step of detection of the crack.

11. The method as claimed in claim 10, wherein the detection of the crack is obtained by implementing, at different points of a zone surrounding the crack, a temporal Fourier transform of the temperature at each point, followed by a calculation of the Laplacian of the amplitude of the sinusoidal component of the temperature at the modulation frequency.

* * * * *